US008478423B2

(12) United States Patent
McDonald et al.

(10) Patent No.: US 8,478,423 B2
(45) Date of Patent: Jul. 2, 2013

(54) INSULATOR LAYERS FOR LEADS OF IMPLANTABLE ELECTRIC STIMULATION SYSTEMS AND METHODS OF MAKING AND USING

(75) Inventors: Matthew Lee McDonald, Glendale, CA (US); Anne Margaret Pianca, Santa Monica, CA (US); Ross Daniel Venook, Burlingame, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 197 days.

(21) Appl. No.: 12/419,738

(22) Filed: Apr. 7, 2009

(65) Prior Publication Data

US 2010/0256693 A1 Oct. 7, 2010

(51) Int. Cl.
*A61N 1/05* (2006.01)
(52) U.S. Cl.
USPC ............ 607/116; 607/63; 600/372; 600/373; 600/377
(58) Field of Classification Search
USPC ............ 607/63, 116–119, 121, 122; 600/377; 174/33, 36, 102 R, 108, 109
See application file for complete search history.

(56) References Cited

U.S. PATENT DOCUMENTS

| 4,154,247 | A |   | 5/1979  | O'Neill         |         |
|-----------|---|---|---------|-----------------|---------|
| 4,559,951 | A | * | 12/1985 | Dahl et al.     | 600/374 |
| 4,870,969 | A |   | 10/1989 | Swartz          |         |
| 5,070,605 | A |   | 12/1991 | Daglow et al.   |         |
| 5,203,348 | A |   | 4/1993  | Dahl et al.     |         |
| 5,217,010 | A |   | 6/1993  | Tsitlik et al.  |         |
| 5,241,957 | A |   | 9/1993  | Camps et al.    |         |
| 5,308,342 | A | * | 5/1994  | Sepetka et al.  | 604/525 |
| 5,330,522 | A | * | 7/1994  | Kreyenhagen     | 607/122 |
| 5,417,208 | A | * | 5/1995  | Winkler         | 600/374 |

(Continued)

FOREIGN PATENT DOCUMENTS

| EP | 92798 A1  | 11/1983 |
| EP | 369044 A1 | 5/1990  |

(Continued)

OTHER PUBLICATIONS

International Search Report and Written Opinion for International Application No. PCT/US2010/028819, Mailed Jun. 10, 2010.

(Continued)

*Primary Examiner* — Carl H Layno
*Assistant Examiner* — Eugene Wu
(74) *Attorney, Agent, or Firm* — Frommer Lawrence & Haug LLP; Patrick R. Turner (57) ABSTRACT

An implantable lead includes a plurality of conductors disposed in an elongated member. At least one of the conductors includes at least one unit that includes a first conductor segment extending along the elongated member from a beginning point to a first position, a second conductor segment extending along the elongated member from the first position to a second position, and a third conductor segment extending from the second position to an endpoint. An inner insulator layer is disposed along at least a portion of the elongated member and is formed of a material that is flowable to fill in at least some open spaces between portions of at least one of the units. An outer insulator layer is disposed over at least a portion of the inner insulator layer. The outer insulator layer has at least one physical characteristic different from the inner insulator layer.

17 Claims, 6 Drawing Sheets

U.S. PATENT DOCUMENTS

| | | | |
|---|---|---|---|
| 5,466,252 A * | 11/1995 | Soukup et al. | 607/116 |
| 5,480,416 A | 1/1996 | Garcia et al. | |
| 5,545,203 A * | 8/1996 | Doan | 607/122 |
| 5,562,722 A | 10/1996 | Racz et al. | |
| 5,571,156 A | 11/1996 | Schmukler | |
| 5,620,476 A | 4/1997 | Truex et al. | |
| 5,628,774 A * | 5/1997 | Helland et al. | 607/116 |
| 5,674,272 A * | 10/1997 | Bush et al. | 607/122 |
| 5,810,725 A | 9/1998 | Sugihara et al. | |
| 6,129,749 A | 10/2000 | Bartig et al. | |
| 6,181,969 B1 | 1/2001 | Gord | |
| 6,289,250 B1 | 9/2001 | Tsuboi et al. | |
| 6,405,091 B1 | 6/2002 | Vachon et al. | |
| 6,506,972 B1 * | 1/2003 | Wang | 174/36 |
| 6,508,804 B2 * | 1/2003 | Sarge et al. | 604/524 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,795,730 B2 * | 9/2004 | Connelly et al. | 607/9 |
| 6,961,622 B2 | 11/2005 | Gilbert | |
| 7,092,766 B1 | 8/2006 | Salys et al. | |
| 7,149,585 B2 * | 12/2006 | Wessman et al. | 607/116 |
| 7,244,150 B1 | 7/2007 | Brase et al. | |
| 7,313,444 B2 | 12/2007 | Pianca et al. | |
| 7,519,432 B2 | 4/2009 | Bolea et al. | |
| 7,555,349 B2 | 6/2009 | Wessman et al. | |
| 2002/0143377 A1 | 10/2002 | Wessman et al. | |
| 2002/0183804 A1 | 12/2002 | Malaney et al. | |
| 2003/0114905 A1 | 6/2003 | Kuzma | |
| 2004/0059392 A1 | 3/2004 | Parramon et al. | |
| 2004/0199069 A1 * | 10/2004 | Connelly et al. | 600/412 |
| 2005/0165465 A1 | 7/2005 | Pianca et al. | |
| 2005/0171587 A1 | 8/2005 | Daglow et al. | |
| 2006/0041294 A1 | 2/2006 | Gray | |
| 2006/0085049 A1 | 4/2006 | Cory et al. | |
| 2006/0122682 A1 | 6/2006 | Sommer et al. | |
| 2006/0265026 A1 | 11/2006 | Madjar et al. | |
| 2006/0265038 A1 * | 11/2006 | Hagen et al. | 607/116 |
| 2007/0043399 A1 | 2/2007 | Stevenson et al. | |
| 2007/0123949 A1 | 5/2007 | Dabney et al. | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0208383 A1 | 9/2007 | Williams | |
| 2007/0219595 A1 | 9/2007 | He | |
| 2007/0239243 A1 | 10/2007 | Moffitt et al. | |
| 2007/0265666 A1 | 11/2007 | Roberts et al. | |
| 2007/0265691 A1 | 11/2007 | Swanson | |
| 2007/0282411 A1 | 12/2007 | Franz et al. | |
| 2007/0299490 A1 | 12/2007 | Yang et al. | |
| 2008/0039709 A1 | 2/2008 | Karmarkar | |
| 2008/0071320 A1 | 3/2008 | Brase | |
| 2008/0103576 A1 | 5/2008 | Gerber | |
| 2008/0119917 A1 * | 5/2008 | Geistert | 607/116 |
| 2008/0172118 A1 | 7/2008 | Johnson et al. | |
| 2008/0262584 A1 * | 10/2008 | Bottomley et al. | 607/119 |
| 2009/0018630 A1 | 1/2009 | Osypka et al. | |
| 2009/0099635 A1 | 4/2009 | Foster | |
| 2009/0125080 A1 | 5/2009 | Montgomery, Jr. | |
| 2010/0114277 A1 * | 5/2010 | Zhao et al. | 607/116 |

FOREIGN PATENT DOCUMENTS

| | | |
|---|---|---|
| EP | 585553 A1 | 3/1994 |
| EP | 1163023 A1 | 12/2001 |
| EP | 1412025 A2 | 4/2004 |
| EP | 1469910 A1 | 10/2004 |
| EP | 1818074 A1 | 8/2007 |
| EP | 1923094 A1 | 5/2008 |
| WO | WO-82/02664 A1 | 8/1982 |
| WO | WO-9308871 A1 | 5/1993 |
| WO | WO-98/17345 A1 | 4/1998 |
| WO | 98/56448 A1 | 12/1998 |
| WO | WO-00/11762 A1 | 3/2000 |
| WO | 01/08738 A1 | 2/2001 |
| WO | WO-2006/130202 A2 | 12/2006 |
| WO | WO-2008/092246 A1 | 8/2008 |
| WO | 2008/115383 A2 | 9/2008 |

OTHER PUBLICATIONS

U.S. Appl. No. 11/238,240, filed Sep. 29, 2005.

* cited by examiner

INSULATOR LAYERS FOR LEADS OF IMPLANTABLE ELECTRIC STIMULATION SYSTEMS AND METHODS OF MAKING AND USING

FIELD

The present invention is directed to the area of implantable electrical stimulation systems and methods of making and using the systems. The present invention is also directed to implantable electrical stimulation leads having multiple layers of material disposed over at least a portion of at least one conductor extending along a length of the lead, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead includes an elongated member having a distal end, a proximal end, and a longitudinal length; a plurality of electrodes disposed on the distal end of the elongated member; a plurality of terminals disposed on the proximal end of the elongated member; and a plurality of conductors each electrically coupling at least one of the electrodes to at least one of the terminals. At least one of the conductors includes at least one unit. The at least one unit includes a first conductor segment, a second conductor segment, and a third conductor segments. The first conductor segment extending along the elongated member from a beginning point to a first position. The second conductor segment extending along the elongated member from the first position to a second position. The third conductor segment extending along the elongated member from the second position to an endpoint. An inner insulator layer is disposed along at least a portion of the elongated member. The inner insulator layer is formed of a material that is flowable when applied to the conductors to fill in at least some open spaces between portions of at least one of the units. An outer insulator layer is disposed over at least a portion of the inner insulator layer. The outer insulator layer has at least one physical characteristic that is different from the inner insulator layer.

In another embodiment, an electrical stimulation system includes an implantable lead, a control module, and a connector for receiving the lead. The implantable lead includes an elongated member having a distal end, a proximal end, and a longitudinal length; a plurality of electrodes disposed on the distal end of the elongated member; a plurality of terminals disposed on the proximal end of the elongated member; and a plurality of conductors each electrically coupling at least one of the electrodes to at least one of the terminals. At least one of the conductors includes at least one unit. The at least one unit includes a first conductor segment, a second conductor segment, and a third conductor segments. The first conductor segment extending along the elongated member from a beginning point to a first position. The second conductor segment extending along the elongated member from the first position to a second position. The third conductor segment extending along the elongated member from the second position to an endpoint. An inner insulator layer is disposed along at least a portion of the elongated member. The inner insulator layer is formed of a material that is flowable when applied to the conductors to fill in at least some open spaces between portions of at least one of the units. An outer insulator layer is disposed over at least a portion of the inner insulator layer. The outer insulator layer has at least one physical characteristic that is different from the inner insulator layer. The control module is configured and arranged to electrically couple to the proximal end of the lead. The control module includes a housing and an electronic subassembly disposed in the housing. The connector has a proximal end, a distal end, and a longitudinal length. The connector is configured and arranged to receive the lead. The connector includes a connector housing and a plurality of connector contacts disposed in the connector housing. The connector housing defines a port at the distal end of the connector that is configured and arranged for receiving the proximal end of the lead. The connector contacts are configured and arranged to couple to at least one of the plurality of terminals disposed on the proximal end of the lead.

In yet another embodiment, a method for forming an implantable lead includes forming an elongated conductor into at least one unit that comprises a first conductor segment, a second conductor segment, and a third conductor segment. The first conductor segment extends in a first direction from a beginning point to a first position. The second conductor segment extends in a second direction that is opposite to the first direction from the first position to a second position. The third conductor segment extends in the first direction from the second position to an endpoint. An inner insulator layer is disposed over at least a portion of the conductor. The inner insulator layer is flowable when applied over the conductor to fill in at least some open spaces between portions of the at least one unit. An outer insulator layer is disposed over at least a portion of the inner insulator layer. The outer insulator has at least one physical characteristic that is different from the inner insulator layer. A first end of the conductor is coupled to an electrode and a second end of the conductor is coupled to a terminal.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having multiple layers of material disposed over at least a portion of at least one conductor extending along a length of the lead, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
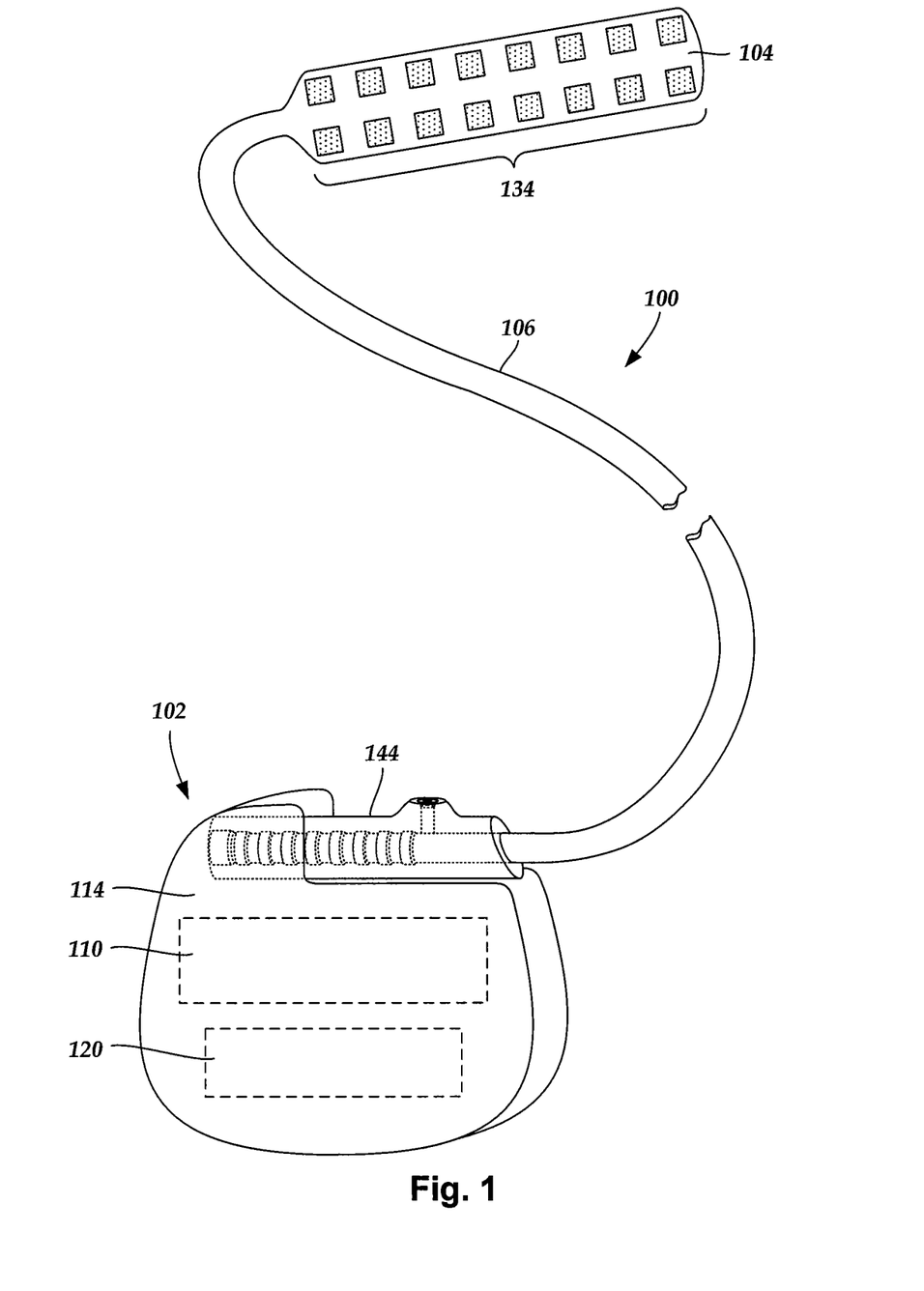
FIG. 1 is a schematic view of one embodiment of an electrical stimulation system, according to the invention.
Figure 2:
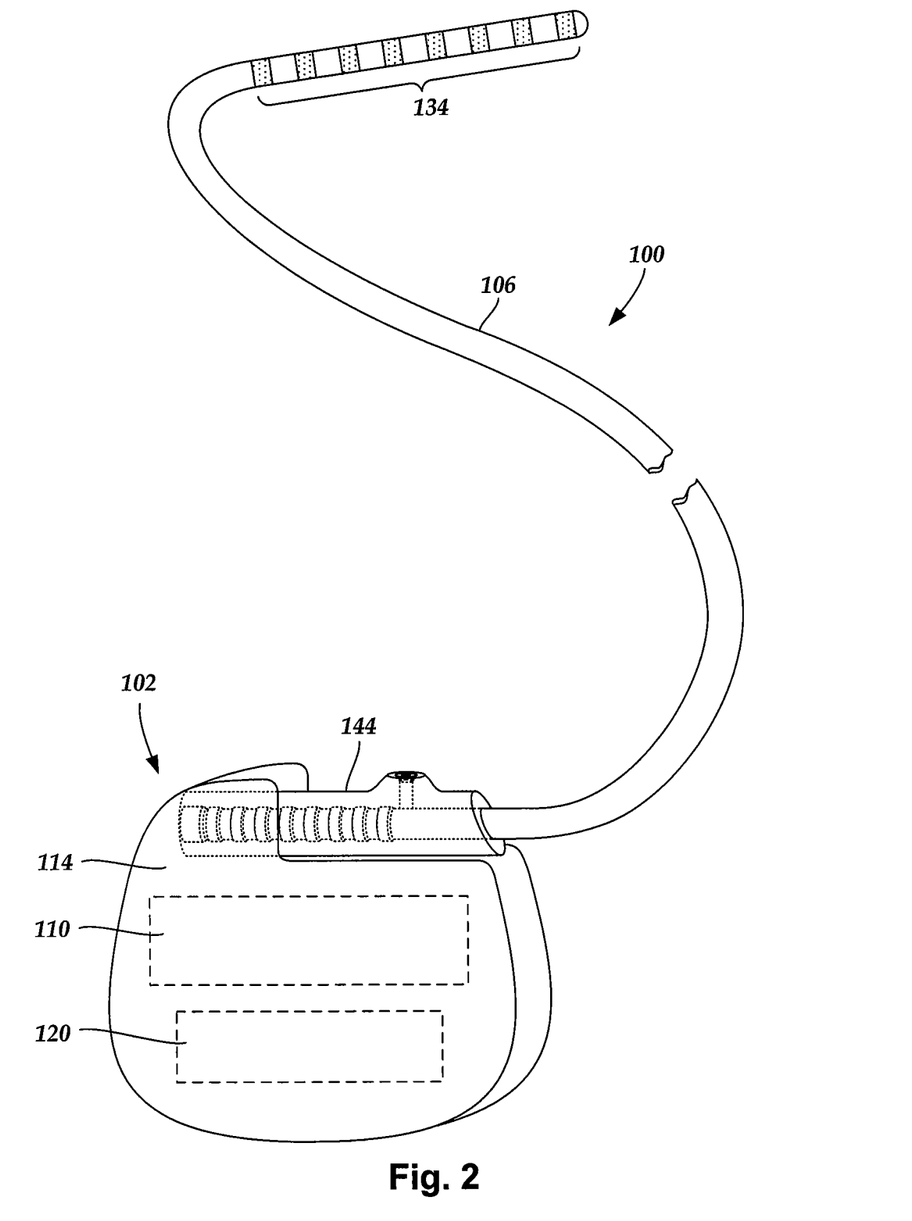
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
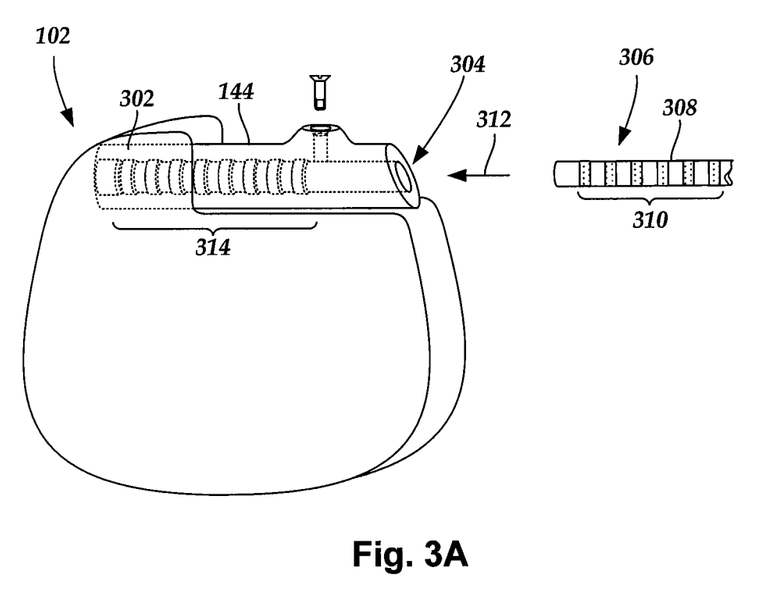
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
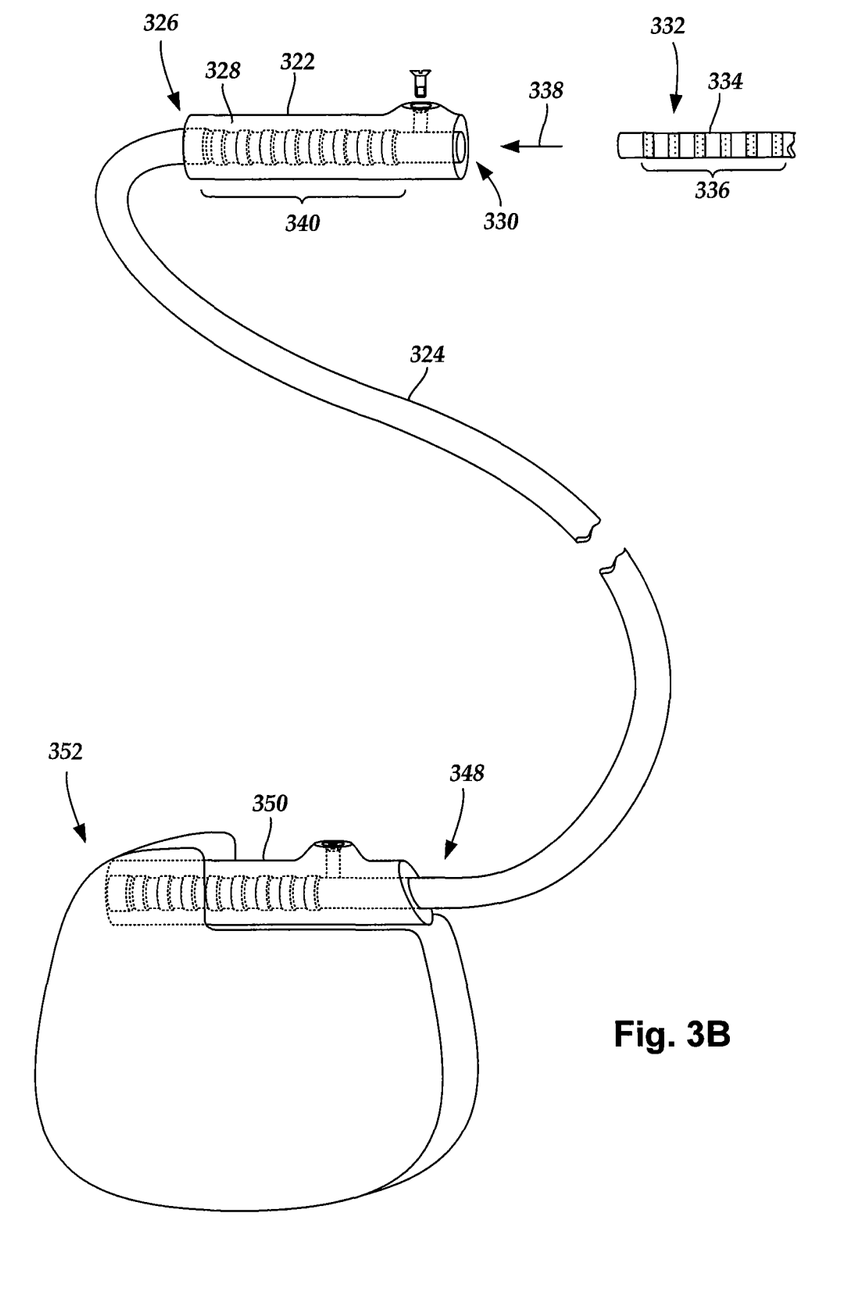
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one terminal to an electrode (or other conductive contact) can be arranged in a conductor path to eliminate or reduce the effect of RF irradiation, such as that generated during magnetic resonance imaging ("MRI"). The conductor path includes a plurality of units arranged in series. In some embodiments, the units are disposed along a single continuous conductor. In other embodiments, the units are separate conductive elements electrically coupled together.

Each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-layer region flanking at least one end of the multi-layer region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight. In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
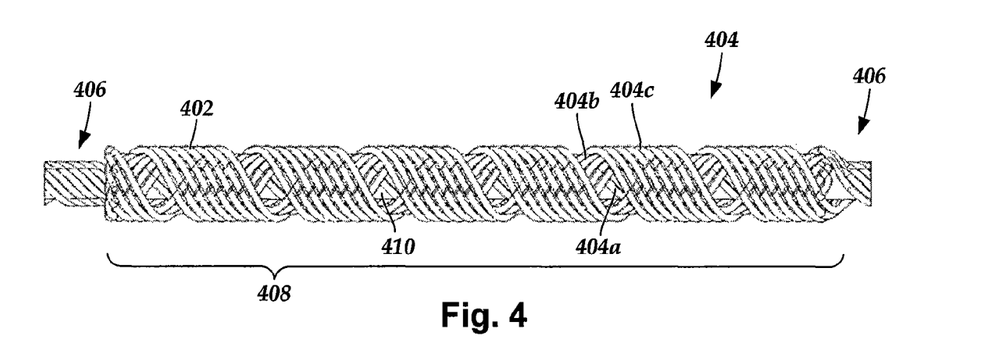
FIG. 4 is a schematic side view of one embodiment of portions of a plurality of conductors disposed along a conductor placement sleeve, the conductors configured into units, according to the invention.

FIG. 4 schematically illustrates one embodiment of a plurality of conductors 402. The conductors 402 are configured into a plurality of units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-layer regions, such as the single-layer regions 406, separated from one another by a multi-layer region, such as the multi-layer region 408.

In at least some embodiments, the conductors 402 are disposed along a conductor placement sleeve 410. The conductor placement sleeve 410 can be formed from any suitable biocompatible material including, for example, one or more polymers. In at least some embodiments, conductor insulation is disposed over the conductors 402 to encapsulate the conductors 402 and electrically isolate the conductors 402 from one another.

In at least some embodiments, one or more conductors having one or more units may be disposed in an elongated member (e.g., a lead or lead extension). In at least some embodiments, the ends of the conductors 402 can be coupled to terminals, electrodes, or conductive contacts. In preferred embodiments, each of the conductors in an elongated member are configured into units. In at least some embodiments, only a subset of the conductors disposed in an elongated member include one or more units, the remaining conductors having a different arrangement (for example, a single conductor segment between the terminal(s) and electrode(s)/conductive contact(s)).

When one or more conductors having one or more units are disposed in an elongated member, the shape of the one or more units may cause one or more open spaces to be formed along a longitudinal length of the elongated member. For example, an elongated member may include one or more open spaces between two or more conductors, between two or more units of the same conductor (e.g., single layer regions 406), between two or more conductor segments of the same unit (e.g., between layers of coils), or between one or more portions of the same conductor segment (e.g. between individual coils).

When a lead is implanted in a patient, it may be important to maintain continuous functioning of the lead within established parameters. Introduction of bodily fluids into the elongated member may alter the performance of the lead which, in turn, may adversely affect a patient. When an elongated member initially contains one or more open spaces, over time bodily fluids may seep into the elongated member and fill the open spaces. Accordingly, it may also be an advantage to attempt to maintain a constant environment within the elongated member by controlling the contents of the empty spaces, by at least one of reducing, or even eliminating, the open spaces in the elongated member, or by filling the empty spaces with one or more substances having known or predictable mechanical or electromagnetic properties.

One way to reduce or eliminate open spaces within the elongated member is to encase the one or more conductors disposed within the elongated member in an insulator layer. Encasing the one or more conductors may also provide additional protection for the conductors from damage from patient movement or to prevent coiled segments of the one or more conductors from unwinding or from moving relative to one another. Encasing the conductors also controls the spacing between adjacent coiled segments and the local environment in which the conductors are disposed.

Encasing the conductors with a single insulator layer may have one or more disadvantages. For example, a single insulator layer may not provide the needed penetration, as well as provide the desired protection or immobilization of the coiled sections. For example, a layer formed from a flowable material may adequately fill the open spaces, but may not provide the durability to protect the one or more conductors from damage or prevent coiled segments from unwinding or from moving relative to one another. Conversely, a layer formed from a non-flowing material may provide the durability to protect the conductors from damage or prevent coiled segments from unwinding or from moving relative to one another, but may not protect open spaces from becoming filled with bodily fluids over the duration of the intended implantation of the lead.

In at least some embodiments, conductors disposed in an elongated member may be encased by multiple insulation layers. In at least some embodiments, each insulation layer may include different materials. In at least some embodiments, each insulation layer may include variations of the same material. For example, one or more substances may be added to a given material under different conditions (e.g., temperature, pressure, or the like) or in different amounts, to change one or more characteristics of the material, such as melting point, durability, rigidity, conductivity, or the like. In another example, two similar materials (e.g., silicone or polyurethane) may differ due to differences in characteristics such as degree of cross-linking or different molecular weight.

In at least some embodiments, conductors are encased by an inner layer and an outer layer. In at least some embodiments, one or more of the conductors also include one or more layers of conductor insulation disposed over at least a portion of the conductor. The one or more layers of conductor insulation are separate from the inner insulation layer or the outer insulation layer. When one or more layers of conductor insulation are disposed over at least a portion of one or more of the conductors, the inner insulation layer is disposed over the one or more layers of conductor insulation.

Figure 5A:
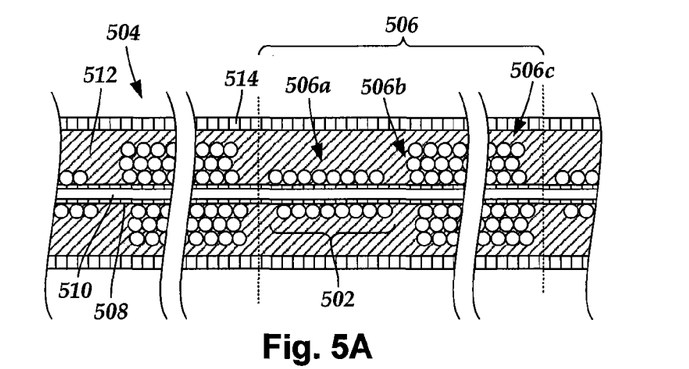
FIG. 5A is a schematic longitudinal cross-sectional view of one embodiment of portions of a plurality of conductors disposed in a portion of an elongated member, the elongated member including inner and outer insulation layers disposed over the conductors, according to the invention.

In at least some embodiments, the one or more conductors are completely encased by the inner insulator layer and the outer insulation layer is disposed over the inner insulation layer. FIG. 5A is a schematic longitudinal cross-sectional view of one embodiment of portions of a plurality of conductors 502 disposed in an elongated member 504. The illustrated portions of the conductors 502 includes unit 506, shown between two vertical dotted lines. Unit 506 includes a first conductor segment 506a, a second conductor segment 506b, and a third conductor segment 506c. In at least some embodiments, the conductors 502 are disposed over a conductor placement sleeve 508. In at least some embodiments, the conductor placement sleeve 508 defines a lumen 510.

Figure 5B:
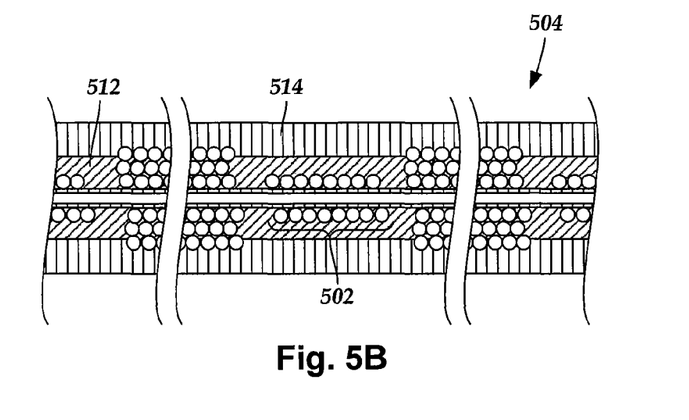
FIG. 5B is a schematic longitudinal cross-sectional view of another embodiment of portions of a plurality of conductors disposed in a portion of an elongated member, the elongated member including inner and outer insulation layers disposed over the conductors, according to the invention.

An inner insulation layer 512 is disposed over the conductors 502. An outer insulation layer 514 is disposed over the inner insulation layer 512. In at least some embodiments, the outer insulation layer 514 is disposed over the inner insulation layer 512 such that the elongated member 504 has a uniform transverse diameter along a longitudinal length of the elongated member 504. In FIG. 5A, the conductors 502 are completely encased in the inner insulation layer 512. FIG. 5B is a schematic longitudinal cross-sectional view of another embodiment of portions of the plurality of conductors 502 disposed in the elongated member 504. In FIG. 5B, the conductors 502 are partially encased in the inner insulation layer 512 and partially encased in the outer insulation layer 514.

In at least some embodiments, the inner insulation layer 512 penetrates and fills empty spaces along a longitudinal length of the elongated member 502 not occupied by the conductors including, for example, spaces between adjacent units, spaces between individual coils of one of the conductor segments, spaces between two or more of the conductors 502.

In at least some embodiments, the inner insulation layer 512 is a flowable material that penetrates and fills in open spaces formed around the conductors 502 disposed in the elongated member 504. In at least some embodiments, the outer insulation layer 514 is a more durable than the inner insulation layer 512. In at least some embodiments, the outer insulation layer 514 is more rigid than the inner insulation layer 512. In at least some embodiments, the outer insulation layer 514 is substantially more rigid than the inner insulation layer 512. In at least some embodiments, the outer insulation layer 514 forms a shell around the inner insulation layer 512.

The inner insulator layer 512 can be formed from any suitable non-conductible, biocompatible material adapted to flow when applied to the elongated member 504 including, for example, silicone elastomers, hydrogels, polyurethane, other thermoplastic polymers, and the like or combinations thereof. In at least some embodiments, the inner insulator layer 512 is formed from a material that may set or cross-link after flowing, for example, as temperature is lowered or when irradiated with light (e.g., visible, ultraviolet, or infrared) or when heated to a cross-linking activation temperature. In at least some embodiments, the inner insulator layer 512 is formed from a doped material, or a composite material (e.g., a material filled with glass, carbon fiber, or the like). In at least some embodiments, the inner insulator layer 512 is a foam. In at least some embodiments, the inner insulator layer 512 is configured and arranged to couple (e.g., adhere, or the like) with one or more of the conductor placement sleeve 508, electrodes (see e.g., 134 of FIG. 1), terminals (see e.g., 310 of FIG. 3A), or conductive contacts (see e.g., 340 of FIG. 3B). In at least some embodiments, the material used to form the inner insulator layer 512 varies along the length of the elongated member 504.

The inner insulator layer 512 may be disposed over and between the conductors 502 using many different techniques or processes including, for example, dip coating, injection molding, or other coating or molding techniques. Other coating and molding techniques may include extrusion, passing an outer sleeve of material (e.g., an outer insulator layer) around the conductors and injecting the inner insulator layer into the sleeve, pre-filling a sleeve with the inner insulator layer and then pulling the filled sleeve over the conductors, or the like or combinations thereof. In at least some embodiments, some of the abovelisted techniques or processes may be performed while placing the conductor in a vacuum to evacuate air pockets or draw material into open spaces.

An outer insulator layer 514 is disposed over at least a portion of the inner insulator layer 512. The outer insulator layer 514 can be formed from any suitable non-conductible, biocompatible material adapted to be non-flowing at temperatures at or below body temperature including, for example, silicone elastomers, hydrogels, other thermoplastic polymers, other thermoset materials, and the like or combinations thereof. Employing an outer insulator layer formed from a thermoplastic may have an advantage of being potentially weldable, either directly or indirectly, to electrodes (see e.g., 134 in FIG. 1) or terminals (see e.g., 310 of FIG. 3A). In at least some embodiments, the outer insulator layer 514 is formed from a doped material, or a composite material (e.g., a material filled with glass, carbon fiber, or the like). In at least some embodiments, the outer insulator layer 514 is configured and arranged to bond with one or more of electrodes (see e.g., 134 of FIG. 1), terminals (see e.g., 310 of FIG. 3A), or conductive contacts (see e.g., 340 of FIG. 3B). In at least some embodiments, the material used to form the outer insulator layer 514 varies along the length of the elongated member 504.

The outer insulator layer 514 may be disposed over the conductors 502 using many different techniques or processes including, for example, dip coating, injection molding, or other coating or molding techniques. Other techniques may include extrusion, reflowing the outer insulator layer using thermal methods (e.g., a sleeve fitted over and then reflowed by heating), and the like or combinations thereof. In at least some embodiments, some of the abovelisted techniques or processes may be performed while placing the conductors 502 in a vacuum to evacuate air pockets.

In at least some embodiments, the outer insulator layer 514 forms a smooth outer surface along at least a portion of the longitudinal length of the elongated member 504. In at least some embodiments, one or more additional layers of material may be utilized in addition to the inner insulator layer 512 and the outer insulator layer 514 including, for example, one or more layers of material between the conductor and the inner insulator layer 512, one or more layers of material between the inner insulator layer 512 and the outer insulator layer 514, or one or more layers of material disposed over the outer insulator layer 514.

It will be understood that an insulator layer may include one or more applications of the same material to the conductors 502 over a period of time. It will also be understood that an insulator layer may include one or more combined parts that collectively form the insulator layer (e.g., two or more combined materials). It will additionally be understood that an insulator layer may, by itself, or by the inclusion one or more additives combined with the one or more materials, effect one or more mechanical properties, or characteristics, of the insulator layers including, for example, rigidity, flexibility, melting point, viscosity, and the like or combinations thereof. In at least some embodiments, the inner insulator layer 512 may serve as a heat shield to protect one or more conductors 502 during subsequent processing steps including, for example, thermoforming the outer insulator layer 514 around the inner insulator layer 512.

In at least some embodiments, the inner insulator layer 512 is more flexible than the outer insulator layer 514. In at least some embodiments, the outer insulator layer 514 is more flexible than the inner insulator layer 512. In at least some embodiments, the flexibility of the elongated member 504 may be adjusted by varying the flexibility of either, or both, the inner insulator layer 512 or the outer insulator layer 514. In at least some embodiments, the combination of materials used to form the inner insulator layer 512 and the outer insulator layer 514 improve the flex fatigue properties of the elongated member 504. In other words, in at least some embodiments, the combination of materials used to form the inner insulator layer 512 and the outer insulator layer 514 may collectively reduce the forces transmitted to the conductors 502, as compared to conventional jacketing material.

It will be understood that an insulator layer may, by itself, or by the inclusion one or more additives combined with the one or more materials, effect one or more electromagnetic properties, or characteristics, of the insulator layers including, for example, conductance, inductance, capacitance, or the like. In at least some embodiments, one or more of the conductance, inductance, or capacitance properties are only altered when exposed to certain frequency ranges. For example, in at least some embodiments, one or more of the conductance, inductance, or capacitance properties are only altered when exposed to frequency ranges at or around frequencies used during MRI procedures (e.g., 64 MHz, 128 MHz, or the like).

In at least some embodiments, the inner insulator layer 512 may be modified, or may include one or more materials, for eliminating or reducing the effect of RF radiation on the one or more conductors 502. For example, the inner insulator layer 512 may be modified, or may include one or more-materials, for altering one or more of the dielectric properties (e.g., capacitance or the inductance) of the one or more conductors 502. In at least some embodiments, at least one of the insulator layers can be made lossy, such as by inclusion of conductive elements, thereby lowering resonant behavior of currents flowing in one or more encased conductors 502.

Figure 6:
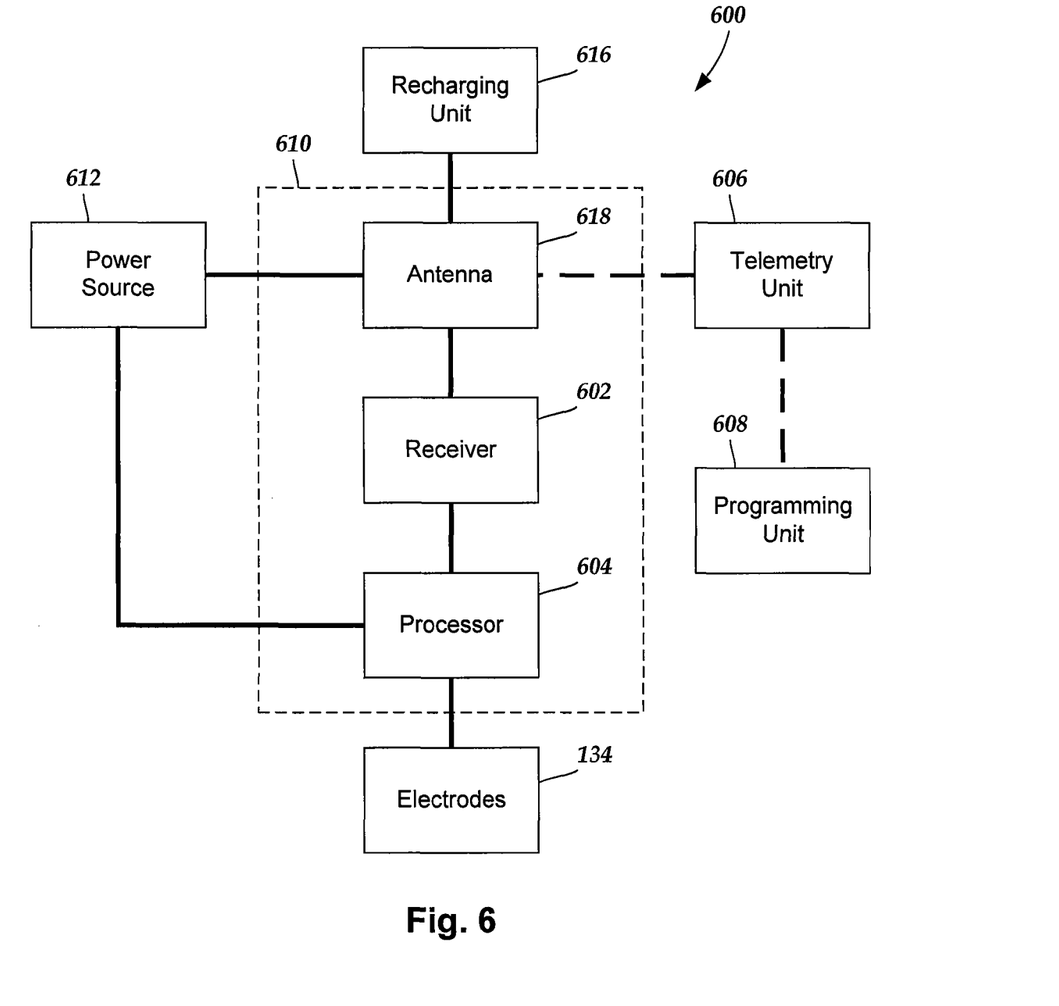
FIG. 6 is a schematic overview of one embodiment of components of a stimulation system, including an electronic subassembly disposed within a control module, according to the invention.

FIG. 6 is a schematic overview of one embodiment of components of an electrical stimulation system 600 including an electronic subassembly 610 disposed within a control module. It will be understood that the electrical stimulation system can include more, fewer, or different components and can have a variety of different configurations including those configurations disclosed in the stimulator references cited herein.

Some of the components (for example, power source 612, antenna 618, receiver 602, and processor 604) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 604 is generally included to control the timing and electrical characteristics of the electrical stimulation system. For example, the processor 604 can, if desired, control one or more of the timing, frequency, strength, duration, and waveform of the pulses. In addition, the processor 604 can select which electrodes can be used to provide stimulation, if desired. In some embodiments, the processor 604 may select which electrode(s) are cathodes and which electrode(s) are anodes. In some embodiments, the processor 604 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (e.g., RF signals) from an external telemetry unit 606 which is programmed by a programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and receiver 602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 600 to cease operation, to start operation, to start charging the battery, or to stop charging the battery. In other embodiments, the stimulation system does not include an antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead comprising:
   an elongated member having a distal end portion, a proximal end portion, and a longitudinal length;
   a plurality of electrodes disposed along the distal end portion of the elongated member;

a plurality of terminals disposed along the proximal end portion of the elongated member;

a plurality of conductors, each conductor electrically coupling at least one of the electrodes to at least one of the terminals, wherein at least one of the conductors comprises at least one unit, the at least one unit comprising a first conductor segment extending along the elongated member from a beginning point to a first position, a second conductor segment extending along the elongated member from the first position to a second position, and a third conductor segment extending along the elongated member from the second position to an endpoint, wherein the first position is between the second position and the endpoint, and the second position is between the beginning point and the first position, wherein the conductor segments are arranged so as to form a plurality of single-coil regions and a plurality of multi-coil regions, wherein the plurality of single-coil regions and the plurality of multi-coil regions are arranged along the longitudinal length of the elongated member in an axially alternating configuration with each individual single-coil region of the plurality of single-coil regions abutted by at least one multi-coil region of the plurality of multi-coil regions;

an inner insulator layer disposed along the entire longitudinal length of the elongated member between the plurality of electrodes and the plurality of terminals, wherein the inner insulator layer is formed of a material that has a first melting point and that is flowable when applied to the conductors to fill in at least some open spaces between portions of at least one of the units; and an outer insulator layer disposed over the inner insulator layer along the entire longitudinal length of the elongated member between the plurality of electrodes and the plurality of terminals, wherein the outer insulator layer has a second melting point;

wherein at least one of the inner insulator layer or the outer insulator layer is formed from a doped material;

wherein each of the plurality of single-coil regions is completely encased by the inner insulation layer;

wherein each of the plurality of multi-coil regions is partially encased in the inner insulation layer and partially encased in the outer insulation layer;

wherein the first melting point is different from the second melting point.

2. The lead of claim 1, wherein a conductor insulation is disposed over at least a portion of at least one of the plurality of conductors, the conductor insulation disposed between the conductor and at least one of the inner insulation layer of the outer insulation layer.

3. The lead of claim 1, wherein the inner insulator layer is configured and arranged to set or cross-link when cooled after flowing.

4. The lead of claim 1, wherein each of the conductor segments is coiled.

5. The lead of claim 1, wherein at least one of the inner insulator layer or the outer insulator layer comprises a foam.

6. The lead of claim 1, wherein the outer insulator layer has an outer surface that extends along the longitudinal length of the elongated member from the distal end of the elongated member to one of the plurality of terminals, the outer surface having a uniform transverse diameter.

7. The lead of claim 1, wherein the outer insulator layer differs from the inner insulator layer by at least one of flexibility or viscosity.

8. The lead of claim 1, wherein the outer insulator layer is formed from a different material than the inner insulator layer.

9. The lead of claim 1, wherein the outer insulation layer is more rigid than the inner insulator layer.

10. The lead of claim 1, wherein the inner insulator layer comprises glass.

11. The lead of claim 1, wherein the outer insulator layer comprises glass.

12. The lead of claim 1, wherein the inner insulator layer is formed from a doped material that comprises at least one conductive element configured and arranged for lowering resonant behavior of current when current propagates along at least one of the plurality of conductors.

13. The lead of claim 1, wherein the outer insulator layer is formed from a doped material that comprises at least one conductive element configured and arranged for lowering resonant behavior of current when current propagates along at least one of the plurality of conductors.

14. An electrical stimulating system comprising:
the lead of claim 1,
a control module configured and arranged to electrically couple to the proximal end of the lead, the control module comprising
a housing, and
an electronic subassembly disposed in the housing; and
a connector for receiving the lead, the connector having a proximal end, a distal end, and a longitudinal length, the connector comprising
a connector housing defining a port at the distal end of the connector, the port configured and arranged for receiving the proximal end of the lead, and
a plurality of connector contacts disposed in the connector housing, the connector contacts configured and arranged to couple to at least one of the plurality of terminals disposed on the proximal end of the lead.

15. The electrical stimulating system of claim 14, wherein the connector is disposed on the control module.

16. The electrical stimulating system of claim 14, further comprising a lead extension having a proximal end and a distal end, the connector disposed on the distal end of the lead extension.

17. The electrical stimulating system of claim 16, wherein the lead extension has a distal end, a proximal end, and a longitudinal length, the lead extension comprising a plurality of conductive contacts disposed on the distal end of the lead extension;

a plurality of terminals disposed on the proximal end of the lead extension;

a plurality of lead extension conductors, each lead extension conductor electrically coupling at least one of the conductive contacts to at least one of the terminals, wherein at least one of the lead extension conductors comprises at least one lead extension conductor unit, the at least one lead extension conductor unit comprising a first lead extension conductor segment extending along the lead extension from a beginning point to a first position, a second lead extension conductor segment extending along the lead extension from the first position to a second position, and a third lead extension conductor segment extending along the lead extension from the second position to an endpoint, wherein the first position is between the second position and the endpoint, and the second position is between the beginning point and the first position;

an inner insulator layer disposed along at least a portion of the lead extension, wherein the inner insulator layer is formed of a material that is flowabie when applied to the lead extension conductors to fill in at least some open spaces between portions of at least one of the lead extension conductor units; and an outer insulator layer disposed over at least a portion of the inner insulator layer, wherein the outer insulator layer has at least one physical characteristic that is different from the inner insulator layer;

wherein at least one of the inner insulator layer or the outer insulator layer is formed from at least one of a doped material or a composite material.

* * * * *